(12) United States Patent
Sattler et al.

(10) Patent No.: US 7,236,986 B1
(45) Date of Patent: Jun. 26, 2007

(54) BILLING SUPPORT IN A HIGH THROUGHPUT COMPUTER-AIDED DETECTION ENVIRONMENT

(75) Inventors: Jason Sattler, Beavercreek, OH (US); Anne C. Marquett, Dayton, OH (US)

(73) Assignee: iCAD, Inc., Beavercreek, OH (US)

( * ) Notice: Subject to any disclaimer, the term of this patent is extended or adjusted under 35 U.S.C. 154(b) by 428 days.

(21) Appl. No.: 10/298,317

(22) Filed: Nov. 18, 2002

Related U.S. Application Data

(60) Provisional application No. 60/333,807, filed on Nov. 20, 2001.

(51) Int. Cl.
*G06F 17/30* (2006.01)

(52) U.S. Cl. .............. 707/104.1; 705/2; 705/3

(58) Field of Classification Search .............. 707/3, 707/9, 104.1, 102; 705/2, 3
See application file for complete search history.

(56) References Cited

U.S. PATENT DOCUMENTS

| | | | |
|---|---|---|---|
| 5,235,510 A | | 8/1993 | Yamada et al. |
| 5,873,094 A | * | 2/1999 | Talatik ............. 707/104.1 |
| 5,917,929 A | * | 6/1999 | Marshall et al. ........ 382/128 |
| 6,006,191 A | * | 12/1999 | DiRienzo ................. 705/2 |
| 6,115,488 A | | 9/2000 | Rogers et al. |
| 2001/0041991 A1 | * | 11/2001 | Segal et al. .............. 705/3 |
| 2002/0133503 A1 | * | 9/2002 | Amar et al. .......... 707/104.1 |
| 2003/0212576 A1 | * | 11/2003 | Kim ......................... 705/2 |
| 2004/0010422 A1 | * | 1/2004 | Michalski et al. ......... 705/2 |

FOREIGN PATENT DOCUMENTS

WO     WO 02/45437 A2      6/2002

* cited by examiner

*Primary Examiner*—Leslie Wong
(74) *Attorney, Agent, or Firm*—Dinsmore & Shohl LLP

(57) ABSTRACT

A method for generating billing statements using information relating to patient identification and film images from patients. The method provides a billing output from a CAD system including the steps of performing a processing operation on patient cases with a CAD system and identifying a status associated with the output of the CAD system. The CAD processing status is computed and stored for each case in association with the patient information. A database storing the joint information provides an efficient method for generating billing statements.

7 Claims, 5 Drawing Sheets

```
Billing Statement:   Mon Oct 28 09:16:03 2002

Authorization Number:   411
Overall Processing History:
    Cases Completed:   156
    Cases Cancelled:    10

Stats for October 2002:
        Completed:   106
        Cancelled:     3

Stats for September 2002:
        Completed:    50
        Cancelled:     7

Hardware/Software Information:
    Build:   5.01g-29802b
    HardDrive ID:   674118925577
```

Figure 5

BILLING SUPPORT IN A HIGH THROUGHPUT COMPUTER-AIDED DETECTION ENVIRONMENT

CROSS-REFERENCE TO RELATED APPLICATIONS

This application claims the benefit of U.S. Provisional application Ser. No. 60/333,807, filed Nov. 20, 2001, incorporated herein by reference.

BACKGROUND OF THE INVENTION

1. Field of the Invention

This invention relates to a method and system for assisting the high throughput use of computer-aided detection systems. One primary aspect of the invention relates to automated billing procedures.

2. Discussion of Related Prior Art

In 2001 an estimated 239,300 women were diagnosed with breast cancer and 40,200 women died from it. Mammography, along with physical examination, is the current procedure of choice for breast cancer screening. Screening mammography has been responsible for an estimated 30 to 35 percent reduction in breast cancer mortality rates. Although mammography is the preferred means of breast cancer screening, it is not perfect. Ten to thirty percent of women diagnosed with breast cancer have their mammograms interpreted as negative. Furthermore, of the malignancies missed by radiologists, an estimated two-thirds are retrospectively evident in the screening mammograms. Missed detections may be attributed to several factors including: poor image quality, interpretation error, lesion obscuration, subtle nature of radiographic findings, eye fatigue, or oversight.

To increase sensitivity, a double reading has been suggested. However, the additional time and expense of a second radiologist makes this option unlikely. Alternatively, a computer-aided diagnosis system may act as a "second reader" to assist the radiologist in detecting and diagnosing lesions. Computer-aided second reading systems, such as the commercially available Second Look® CAD system ($CAD_x$ Systems, Beavercreek, Ohio) have been clinically proven to decrease the rate of missed cancers. Thus, the computer-aided second reading clearly benefits women and their families.

The promise of earlier detection has made many women choose centers providing CAD services. The U.S. government encourages the purchase and use of CAD systems by providing reimbursement to radiologists or hospitals using such systems. In the four and a half years of commercial availability, approximately 5 million women have had their mammograms processed by CAD systems. As the number of cases continues to increase, automated methods for efficient processing and billing for CAD services are essential.

An overview of the typical workflow a mammography center is now provided. A radiology technologist enters patient identification information into an electronic system. Then, the technologist positions the patient in the mammography x-ray device and exposes four films, collectively referred to as a case. The films include two views of each breast, the cranio-caudal and medial-lateral oblique. Before development, patient information may be "flashed" onto the films. They are then developed and inspected to ensure compliance with the Mammographic Quality Standards Act (MQSA). MQSA compliant cases are then loaded into the digitizer of the CAD system by the radiology technician. The technologist uses interface devices such as a keyboard, mouse, touch screen, or speech recognition application to control the CAD system operation and input patient identification information. The digitizer feeds the films one at a time, creating a set of four digital images from a typical case. These digital images are analyzed for signs of cancer by algorithms in the CAD system.

The CAD system produces a visual or textual indication of the location and type of cancer indicator suspected. The output is typically either a printed page or electronic file consisting of the digital mammogram images with suspicious regions highlighted by markers; different marker styles are used to denote different indicators of cancer. When the CAD output is a printed page, it may be stored with the films. When the CAD output is an electronic file, it is stored and recorded such that it may be recalled from patient identification information and printed or displayed on a monitor. The radiologist subsequently uses the CAD output during an interpretation phase. The procedure for incorporating CAD system outputs is given in U.S. Pat. No. 6,115,488, herein incorporated by reference.

To maximize technologist productivity and efficiency, it is desirable to accumulate a number of cases before processing. Typically, the number of accumulated cases requires an overnight's amount of time to process. The collection of films is loaded into the digitizer, patient information is entered, and commands issued to the CAD system to begin processing in the "batch" mode. The cases are processed overnight, producing a collection of CAD outputs. The next morning, the processing is complete. Currently, the average time required to process a standard four-film case is approximately 4-6 minutes. Assuming 14 hours available in an overnight interval, 210 to 140 cases may be processed in an otherwise unused time span. For systems creating paper output, the pages are associated with the proper films for subsequent use by a radiologist.

Batch operation has the disadvantage of being dependent on perfect feeding of films through the digitizer. A common feed error in digitizers is the "double feed" where two films are pulled through the system as one. Mechanisms for sticking include static electricity and film-to-film suction. In a system that relies only upon an input number of films in a case and a digitizer counting the number of digitizer feed commands, the double feed error can cause a misassociation of patient information with CAD system output. To prevent this misassociation, an operator may monitor the processing, stop the processing when a double feed is observed, reload the affected films, and re-start the processing. This is clearly an inefficient use operator time. Alternatively, the CAD system may detect the double feed error, and stop the batch processing. This has the undesirable effect of delaying the night's processing until the operator corrects the situation the following morning. Another aspect of a high throughput CAD environment related to billing CAD providers are reimbursed for their service. Accurate reporting of the number of successfully processed cases are therefore necessary. Additionally, when a CAD system is leased, the owners of the CAD system are paid for each case successfully processed. It is clearly desirable to provide a system and method for efficient generation of billing reports.

SUMMARY OF THE INVENTION

In the above high volume CAD environment, many cases are regularly processed. Patient information is entered and stored. Furthermore CAD processing status is computed and stored for each case in association with the patient information. A database storing the joint information provides an efficient method for generating billing statements.

Accordingly, it is an object of this invention is to provide a method and system for automated billing statement generation in a high-volume CAD environment.

In one aspect of the invention, a method is provided for providing a billing output from a CAD system comprising the steps of: performing a processing operation on at least one case with a CAD system; identifying a status associated with the output of the CAD system; storing information corresponding to the status in a searchable format; inputting a search query for retrieval of stored information matching the search query; and incorporating the retrieved information in a billing statement.

In another aspect of the invention, a method is provided for monitoring a workflow in a system comprising the steps of: obtaining a first list corresponding to patients registered for a service; obtaining a second list corresponding to successful completion of the service for the patients; and comparing the first and second lists and identifying discrepancies.

Other objects will be readily perceived from the following description, claims, and drawings.

BRIEF DESCRIPTION OF THE DRAWINGS

FIG. 5 is an example of a billing statement.

DETAILED DESCRIPTION OF THE PREFERRED EMBODIMENT

Overview

Figure 1:
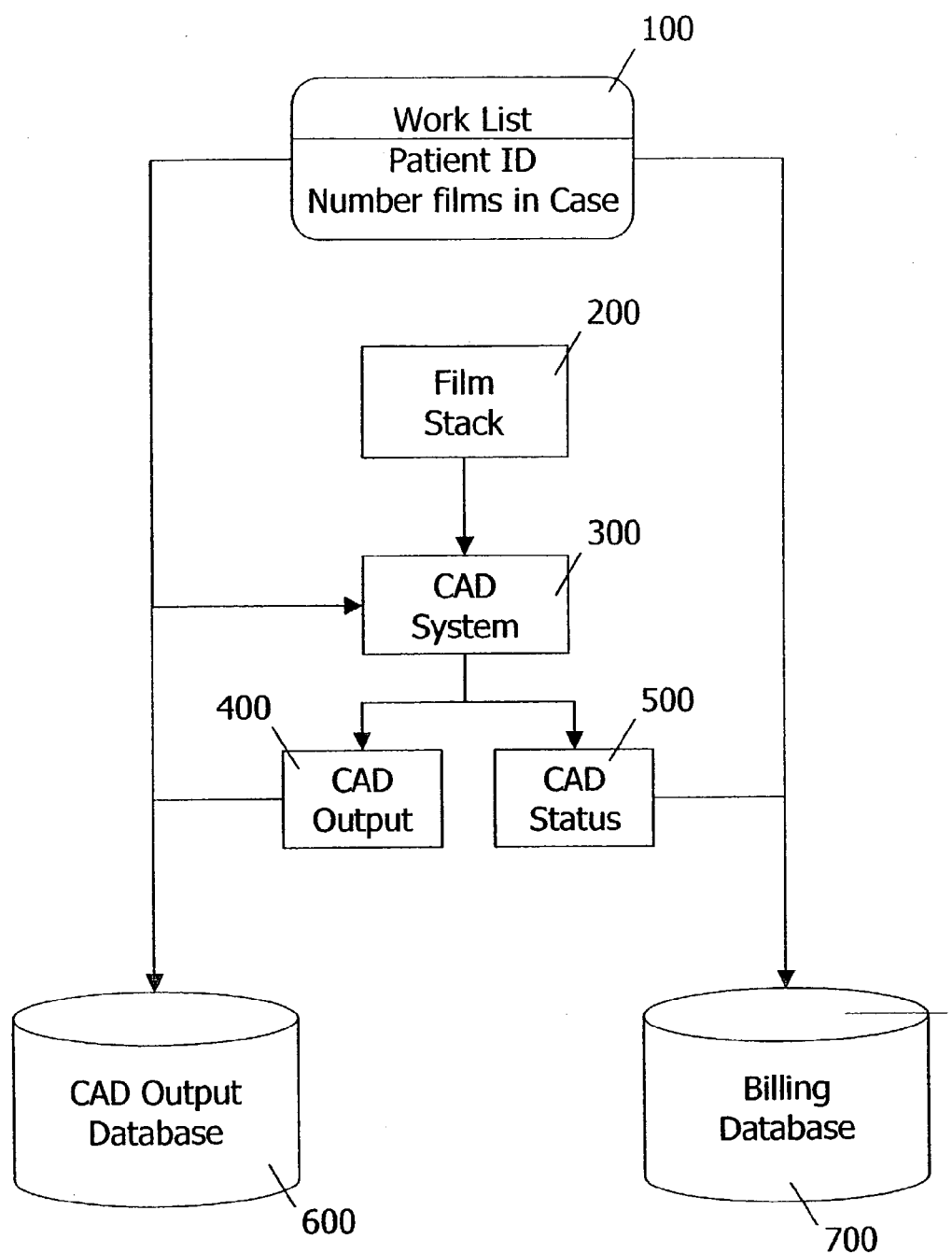
FIG. 1 is an overview of the system.

FIG. 1 shows an overview of the high throughput CAD system. Patient identification information and the number of films for that patient's case are entered in a work list, 100. The work list typically contains information regarding a plurality of patients. The films associated with the patients are combined to form an input film stack, 200. The film stack is input to a CAD system, 300, along with associated patient information from the work list. The patient information includes the number of mammographic images in that patient's case. The CAD system processes digital versions of the mammographic films and then produces a CAD output, 400. The system creates an electronic CAD output that may be displayed on monitor, printed, or stored for subsequent use. The electronic CAD output is stored with patient ID information in a CAD output database, 600. The processing status of each case is determined in step 500 and stored with patient ID information in a billing database, 700. Although this embodiment shows the databases as separate entities, in an alternative embodiment, a single database may be used to store and access both the actual CAD output and the CAD status information.

Figure 2:
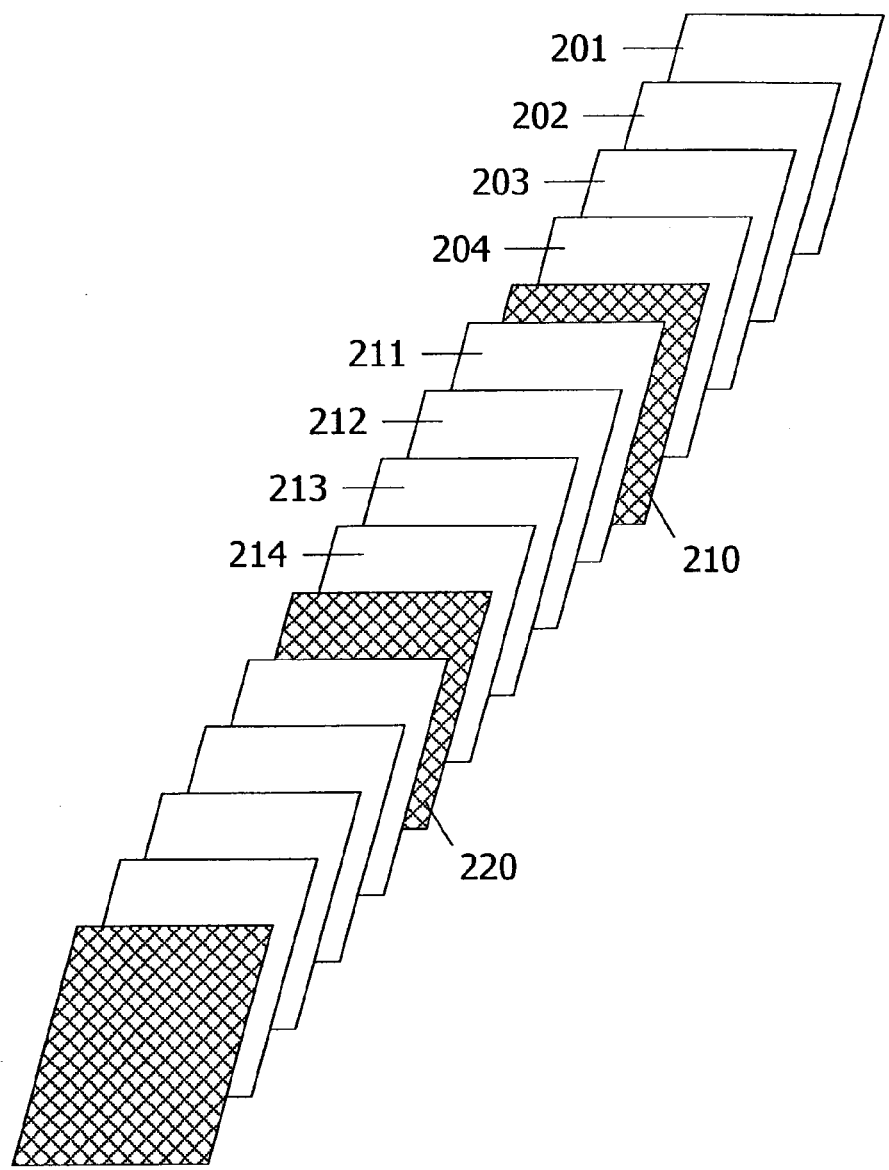
FIG. 2 is an example of a film stack.

An example of an input film stack is shown in FIG. 2. The input stack consists of the first patient's mammography images, 201, 202, 203, and 204; a case separator, 210; the second patient's mammography images, 211, 212, 213, and 214; a case separator, 220, and so on. A case separator is a film with unique markings allowing it to be rapidly and reliably distinguished from a mammographic image.

The key elements in the double feed detection method are the work list and the case separators. The fundamental operation of the double feed detection method is to read the expected number of films in a case from the work list, and then count the number of film feed operations issued until the next case separator is detected. In the error free situation, the number of film feed operations between case separators equals the number of films indicated in the work list. When this occurs, the final case status is reported as "complete". If a case separator is detected with fewer feed operations than the number of films in a case, a double feed error is assumed, and status for the current case is reported as "canceled". Another error mode is the situation of a CAD processing failure on an image. Since CAD systems typically rely on valid CAD output for all images in the case, the case status must be reported as "failed".

Work List

The work list contains patient identification information and the number of film images in the case. Additional information, such as medical history and demographics may also be included.

In one embodiment, an operator enters patient information prior to CAD processing. Alternatively, the CAD system decodes patient information directly from the films; the patient information may then be accumulated during CAD processing. Information associated with the images includes patient name, patient identification number, patient date of birth, initials of technologist, time the output image created, and size of films.

Preferably, the system stores the patient work list information in non-volatile memory such that if the system loses power, the work list information is available after power is restored. This allows for re-starting a batch job without re-entering patient identification information.

The work list may be edited whether or not CAD processing is currently running. That is, patients may be added to the work list while the system is currently running a batch job. The corresponding films are added, in order, to the end of the film stack.

Case Separator

The system distinguishes between the end of one case and the beginning of another via a case separator inserted in the appropriate position of the collection of films in the input batch. In the present invention, a case separator is typically a film exhibiting a unique pattern. The purpose of the pattern is to provide a cue recognizable by the CAD as a case separator and difficult to misrecognize as a medical image. Highly accurate detection of case separators may be obtained by correlating the pattern with the input image. The case separators are positioned between films of different cases. The user inputs the number of films in each patient's case in the work list. This allows the system to detect a digitizer feed error (double feed) or misrecognition of a case separator. Processing may be allowed to proceed after detection of the errors using the knowledge of the number of films in each case as entered by the operator or as determined from on film information.

Error Handling

Figure 3:
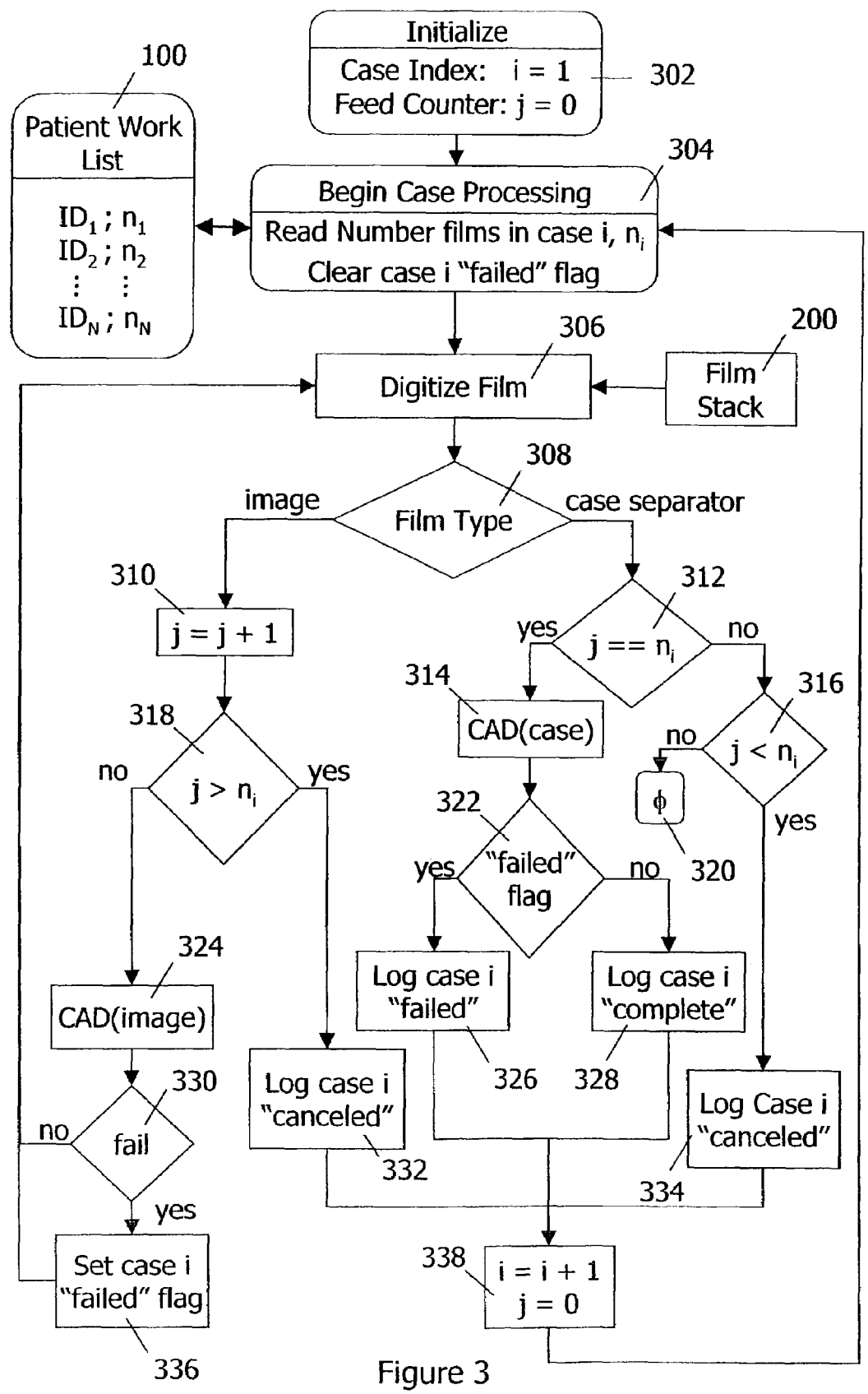
FIG. 3 shows details of double feed detection and error handling logic.

FIG. 3 shows a detailed block diagram of the error handling method of the invention. The lesion detection portion of the CAD is not shown in this figure for clarity. The patient work list, 100, provides patient identification information and the number of films in each patient's case. Upon initialization of batch processing, step 302, the case index is set to one and the feed counter set to zero. Case processing begins in step 304. Here the number of films in case i is read from the work list and stored as $n_i$ and the "failed" flag is cleared. The steps of the figure below step 304 contain decision paths to handle double feed errors and CAD processing failures. For completeness in describing FIG. 3, note step 320 is the null state. That is, given the construction of the algorithm, 320 is a step that cannot occur.

The following sections describe how different error conditions are handled by the system. The desirable result is that this method allows batch processing to continue when feed errors occur. Another desirable result is the creation of a log allowing convenient generation of billing statements.

Each case processed by the CAD system receives a CAD processing status label. In the present invention, the labels are "complete", "canceled", and "failed". Completed cases require no special attention from an operator. However, canceled and failed cases require operator intervention. Both types are typically re-processed by the CAD system. The status labels provide information for the operator to efficiently locate the necessary cases. Double feed errors resulting in canceled cases are unlikely to recur upon re-processing. Cases with a film or films resulting in recurring CAD processing errors may be of interest to CAD system designers.

Error Free Operation

The operation of the error handling method is first described for the error free situation. The next available film from the film stack, 200, is digitized in step 306. The type of film is determined in step 308. The films in the stack must be either a mammographic image or a case separator. Considering the first film to be a mammographic image, the left branch is taken from step 308. The film feed counter is incremented by one in step 310. In step 318, the film feed counter, j, is compared to the number of films in the case, $n_i$, as specified in the work list. If j is less than $n_i$, the digital image is submitted to the CAD system for image based processing, step 324. The image based CAD is assumed to successfully complete, therefore the "failed" flag remains cleared. Step 330 checks the state of the "failed" flag. Since no failure is indicated, the next film in the case is feed through the digitizer in step 306. This sequence of events repeats three more times.

After four feed operations, the feed counter j equals four. The next film digitized will be determined to be a case separator in step 308. In this situation, the right branch is followed from step 308. The feed counter is compared to the number of films in the case in step 312. For this error free example, the feed counter equals the number of films in the case and the left branch taken from step 312. The next step, 314, applies case based CAD processing to the prior $n_i$ films. Next, in step 322, the "failed" flag is checked for the current case. The failed flag is still clear, therefore the right path is taken from step 322 and case i is logged as "complete". In step 338, the case index is incremented and the feed counter reset to zero. Control then returns to step 304 where the batch processing continues.

Double Feed with Two Mammographic Images

The detection of a double feed error is now described. Assume simultaneous feeding of two mammographic images. In this situation, a case separator will be detected in step 308 when the feed counter is less than the number of films specified in the work list. Therefore, the right branch is taken out of step 312 and the bottom branch from step 316. The current case is logged as "canceled" in step 334. In step 338, the case index is incremented and the feed counter reset to zero. Control then returns to step 304 where the batch processing is allowed to continue.

Double Feed with Last Image and Case Separator

In this section, we describe the detection of a double feed error when the films involved are the last image film of a case and a case separator. In this situation, assume the case separator is not detected. This is reasonable assuming the default decision of the case separator detector is "image". When the films are double fed, it is unlikely that the unique pattern of the case separator will be found. Assume the case with index i* has four images, $n_{i*}=4$, and processes the first three films without error.

The double feed then occurs, pulling the fourth film and the case separator. In step 308, the film type is declared "image". In step 310, the feed counter is incremented from three to four. The feed counter is still less than the number of films in the case as specified in the work list, so the left branch is taken out of step 318. Assume the image based CAD is successful, so the left branch is followed from step 330. The next film is digitized in step 306 and determined to be an "image" in step 308. The feed counter is now incremented from four to five in step 310. In step 318 the feed counter is compared to the number of films in the case. Thus, the right branch is taken and case i* is logged as "canceled" in step 332. The case index is incremented to i*+1 and the feed counter reset to zero in step 338. Control then returns to step 304 where the batch processing continues. Further assuming error free operation until the detection of the next case separator, step 312 will be entered with the feed counter one less than the number of films given in the work list. Therefore, the right branch of 312 and the bottom branch of 316 will be followed. Case i*+1 is logged as "canceled" in step 334. In step 338, the case index is incremented and the feed counter reset to zero. Control then returns to step 304 where the batch processing is allowed to continue.

Double Feed with Case Separator and First Image

The handling for a double feed error consisting of a case separator and the first image film of a case is now described. Assume the case with index i* has four images, $n_{i*}=4$, and was processed without error prior to the double feed. Therefore, the feed counter equals four. With the double feeding of the case separator and film, step 308 will declare the film type to be "image". The feed counter is incremented to five in step 310 and compared to the number of films in case i at step 318. Since the feed counter is greater than the expected number of films, the right branch is taken and the current case is logged as "canceled" in step 332. The case index is incremented to i*+1 and the feed counter rest to zero in step 338. Control then returns to step 304 where the batch processing continues. Further assuming error free operation until the detection of the next case separator, step 312 will be entered with the feed counter one less than the number of films given in the work list for case index i*+1. Therefore, the right branch of 312 and the bottom branch of 316 will be followed. Case i+1 is logged as "canceled", in step 334. In step 338, the case index is incremented and the feed counter reset to zero. Control then returns to step 304 where the batch processing is allowed to continue.

CAD Processing Failure

Finally, the error handling in the situation of a CAD processing failure is described. Assume the image based CAD in step 324 processes an image film resulting in a CAD failure. In step 330, the bottom path is taken, and the "failed" flag is set in step 336. Assume error free processing until the next case separator is detected in step 308, where the right branch is taken to step 312. The feed counter will equal the number of films in the case, so the left branch is followed to step 314, where case based processing is applied. In step 322, the "failed" flag is checked. Since the flag is set, the left branch is taken and the case is logged as "failed" in step 326. In step 338, the case index is incremented and the feed counter reset to zero. Control then returns to step 304 where the batch processing is allowed to continue.

Billing Support

The billing support system provides an efficient means to obtain information needed for billing. A primary objective of the billing support system is to provide an automated means for generating information needed in a "pay-per-use" environment.

In a pay-per use business model, a user does not own the CAD system. Rather, the CAD system is leased to the user. The user processes cases with the CAD system and agrees to pay a fee to the owner for each successfully completed case.

Additionally, information may be used to ensure services are provided to patients who check in at an office. For example, a patient checks in with a receptionist upon arrival. The patient's name is placed on an "incoming patients" list indicating the patient's films are to be processed by the CAD system. The incoming patients list and the list of successfully processed cases may be cross referenced to identify those patients who expected but did not receive CAD processing.

Figure 4:
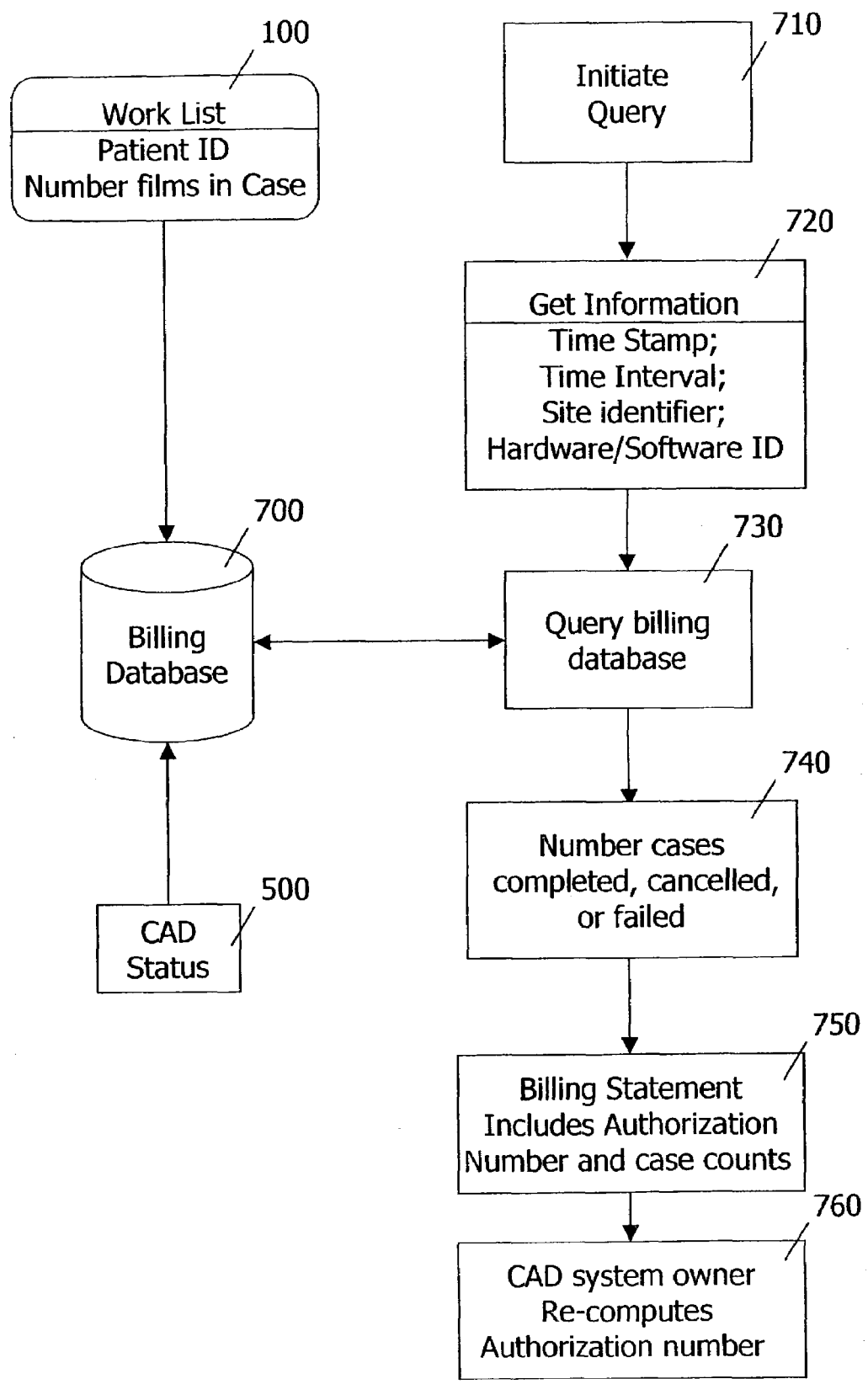
FIG. 4 is a diagram of the method used to generate a billing statement.

A block diagram of the billing support system is shown in FIG. 4. Information from the work list, 100, and CAD processing status, 500, are stored in the billing database, 700. An operator initiates a query to the billing database in step 710. Typically, the query includes a time interval over which to determine the number of successfully processed cases. For example, if an office invoices monthly, the user would specify a one month interval, possibly by selecting a start date and end date. Alternatively, the user may specify a start date and 30 day duration. Step 720 provides information regarding the query. The billing database is queried in step 730, producing a count comprising the number of cases completed, canceled, or failed, 740. This information is provided in a billing statement, 750. The billing statement also includes an authorization number. FIG. 5 is an example of a billing statement.

Referring again to FIG. 4, in step 760 the CAD owner re-computes the authorization number using the predetermined values and information on the billing report. Since the precise function and the predetermined values are unknown to the CAD system users, falsification of billing information in an attempt to avoid full payment will be detectable through an authentication process.

Authorization Number Generation

The authorization number is used to identify inaccurate billing statements. The number of cases successfully processed and additional information is input to a predetermined function. Additional input to the function may be obtained from hardware specific identification numbers for devices within the CAD system. Further inputs affecting the authorization number may be predetermined parameters, including time and date information. When the CAD system owner receives the billing statement, the authorization number is recomputed. If the authorization number on the billing statement does not equal the recomputed value, the received billing statement is rejected. The CAD system owner then takes appropriate actions.

An example of generating an authorization number is now provided. Let the input information be the predetermined input values and the number of successfully completed cases. Assume the predetermined values are the hard drive identification number and the time stamp, in binary numeric format. The number of cases processed is also represented as a binary number. For clarity, this example assumes 6-bit binary numbers. In practice, more bits are required to represent the numbers.

Let the binary date, D, equal '101101', the binary hard drive identification, H, equal '011100', and the number of cases successfully completed, N, equal 53. Further, let the function be $$f(D, H, N) = \left\lfloor \frac{D\|H]_{10} \cdot 37}{N} \right\rfloor \mod 999 \quad (1)$$

where
$\|$ denotes logical OR;
$\lfloor \cdot \rfloor$ denotes rounding down to nearest integer;
$[\cdot]$ denotes conversion to base 10; and
mod denotes the modulus operator.

With the given values for D, H, and N, Eq 1 becomes $$f(D, H, N) = \left\lfloor \frac{[111101]_{10} \cdot 37}{53} \right\rfloor \mod 9999$$
$$= \left\lfloor \frac{61 \cdot 37}{53} \right\rfloor \mod 999$$
$$f(D, H, N) = 42$$

Therefore, the authorization number in this example is 42 and will be stored as part of the billing statement. If the submitted billing statement were altered such that N becomes 35, the re-computed authorization number becomes $$= \left\lfloor \frac{61 \cdot 37}{35} \right\rfloor \mod 999$$
$$f(D, H, N) = 64$$

which does not match the original authorization number on the billing statement.

It can be seen from the above description that the present invention provides an efficient system and method for monitoring the use of a CAD system and billing accordingly.

We claim:

1. A method of providing a billing output from a Computer-Aided Detection (CAD) system comprising the steps of:

performing an automated batch processing operation on at least one case with the CAD system, wherein the automated batch processing continues even after errors occur in the processing;

identifying a status corresponding to successful/unsuccessful processing of the at least one case;

associating the status with the output of the CAD system;

storing information corresponding to the status in a searchable format;

inputting a search query for retrieval of stored information matching the search query;

incorporating the retrieved information in the billing statement; and billing only for the processing with the successful processing status associated with it.

2. The method of claim 1 wherein data corresponding to successful/unsuccessful processing of the at least one case affects the billing statement.

3. The method of claim 2 wherein multiple case are processed and the number of cases that result in successful/unsuccessful processing affect the billing statement.

4. The method of claim 1 wherein the search query corresponds to a time period.

5. The method of claim 1 wherein the output includes an authentication.

6. The method of claim 5 wherein the authentication comprises an authorization number.

7. The method of claim 5 wherein multiple cases are processed and the authorization number is determined based on the number of cases with successful/unsuccessful processing and at least one other affecting factor.

* * * * *